United States Patent [19]

Bailey

[11] Plant 4,854

[45] Jun. 1, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,373

[22] Filed: Sep. 8, 1980

[51] Int. Cl.[3] ..... A01H 5/00

[52] U.S. Cl. ..... Plt./22

[58] Field of Search ..... Plt./22

*Primary Examiner*—James R. Feyrer

*Attorney, Agent, or Firm*—Vincent G. Gioia

[57] ABSTRACT

A new floribunda rose variety of yellow and orange red coloring.

1 Drawing Figure

1

The present invention relates to a new and distinct variety of rose plant of the floribunda rose class, which was originated by my crossing as seed parent the rose known as "Granada" and the rose known as "Queen Elizabeth" as pollen parent.

Among the novel characteristics possessed by this new variety which distinguish it from its parents and all other varieties of which I am aware are very pointed Chinese yellow buds which open to reveal an orange red petal top surface coloring and a very vigorous spreading plant which attains good size. Flowers are exceptionally bright and eye catching. Asexual reproduction by budding of the new variety as performed in Kern County, Calif., shows that the foregoing and other distinguishing characteristics come true to form and are established and transmitted through succeeding propagations.

The new and improved rose variety which I have developed is a fine large flowered floribunda rose bearing blooms singly and in clusters displayed on a vigorous spreading, free branching plant with abundant disease resistant foliage. The plant repeats flowering on a short blooming cycle.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "20B" is plate 20B of the Royal Horticultural Society Color Chart.

Parentage: Seedling.

*Seed parent.*—"Granada".

*Pollen parent.*—"Queen Elizabeth".

Class: Floribunda.

The following observations are made of specimens grown outdoors in Kern County, Calif., during the month of November.

1. FLOWER

Blooming habit: Continuous on a short blooming cycle.

A. Bud (1) *Size.*—Small.

(2) *Form.*—Pointed.

2

(3) *Color.*—Bud color after sepals fall is Chinese yellow 20B with bud tips showing 34B. Some buds show thin edge of 34D which may be petal top surface color bleeding through. Some veining may be also visible.

(4) *Sepals.*—Thin, pointed extending well beyond bud.

(5) *Peduncle.*—Length — $2\frac{1}{2}$ to 3 inches. Aspect — straight, smooth. Strength — erect. Color — near 147A.

B. Bloom:

(1) *Size.*—Average size when fully expanded — about $3\frac{1}{3}$ to 4 inches.

(2) *Borne.*—Singly and several together in clusters.

(3) *Form.*—High centered at first becoming flat, petals loosely roll outward.

(4) *Petalage.*—Number of petals under normal conditions about 22 to 24.

(5) *Color.*—As buds mature and petals unfurl, the petal top surface coloring 34C is seen and the Chinese yellow coloring lightens slightly to 20C, however veining becomes more pronounced and the bleeding of the top surface coloring into the undersurface is more evident at the upper petal edge.

C. Petals:

(1) *Texture.*—Thick.

(2) *Appearance.*—Velvety to satiny.

(3) *Form.*—Oval.

(4) *Arrangement.*—Imbricated.

(5) *Petaloids in center.*—Few.

(6) *Persistence.*—Drop off cleanly.

(7) *Fragrance.*—Slight.

(8) *Lasting quality.*—Good lasting quality.

2. REPRODUCTIVE ORGANS

A. Stamens, filaments and anthers:

(1) *Arrangement.*—Regularly arranged around styles.

(2) *Color.*—21A.

B. Pollen:

*Color.*—13A.

C. Styles: Uniform, medium length.

D. Stigmas:

*Color.*—31B.

E. Hips:

*Shape.*—Globular.

*Size.*—Medium.

*Color.*—26A.

*Do seeds protrude?*—No.

3. PLANT

A. Form: Spreading.

B. Growth: Vigorous, free branching.

*Height attained.*—About 3½ to 4 feet.

C. Foliage: Compound 5 to 7 leaflets.

(1) *Size.*—Medium.

(2) *Quantity.*—Abundant, dense to ground level.

(3) *Color.*—New foliage: upper side — bronze red; under side — near to 59A. Old foliage: upper side — near 137A; under side — near 147B.

(4) *Shape.*—Ovoid.

(5) *Texture.*—Upper side is waxy, leathery and under side is rough, veined.

(6) *Edge.*—Serrated.

(7) *Serration.*—Simple.

(8) *Leaf stem.*—Color — near to 147B. Under side — near 147C.

(9) *Stipules.*—Long, thin.

(10) *Resistance to disease.*—Blackspot — very resistant. Mildew — very resistant.

D. Wood:

(1) *New wood.*—Color — near 146B. Bark — smooth.

(2) *Old wood.*—Color — near 137D. Bark — smooth.

E. Thorns:

(1) *Thorns.*—Quantity (main stalk) — ordinary. On laterals from stalk — few. Form — flat. Length — small. Color — light green with reddish cast. Position — regular.

(2) *Prickles.*—Few.

F. Winter hardiness: Good winter hardiness.

I claim:

1. A new and distinct variety of rose plant of the floribunda class, substantially as shown and described, characterized particularly by very pointed Chinese yellow buds which open to orange red and yellow flowers borne singly and in sprays on a vigorous plant with abundant foliage.

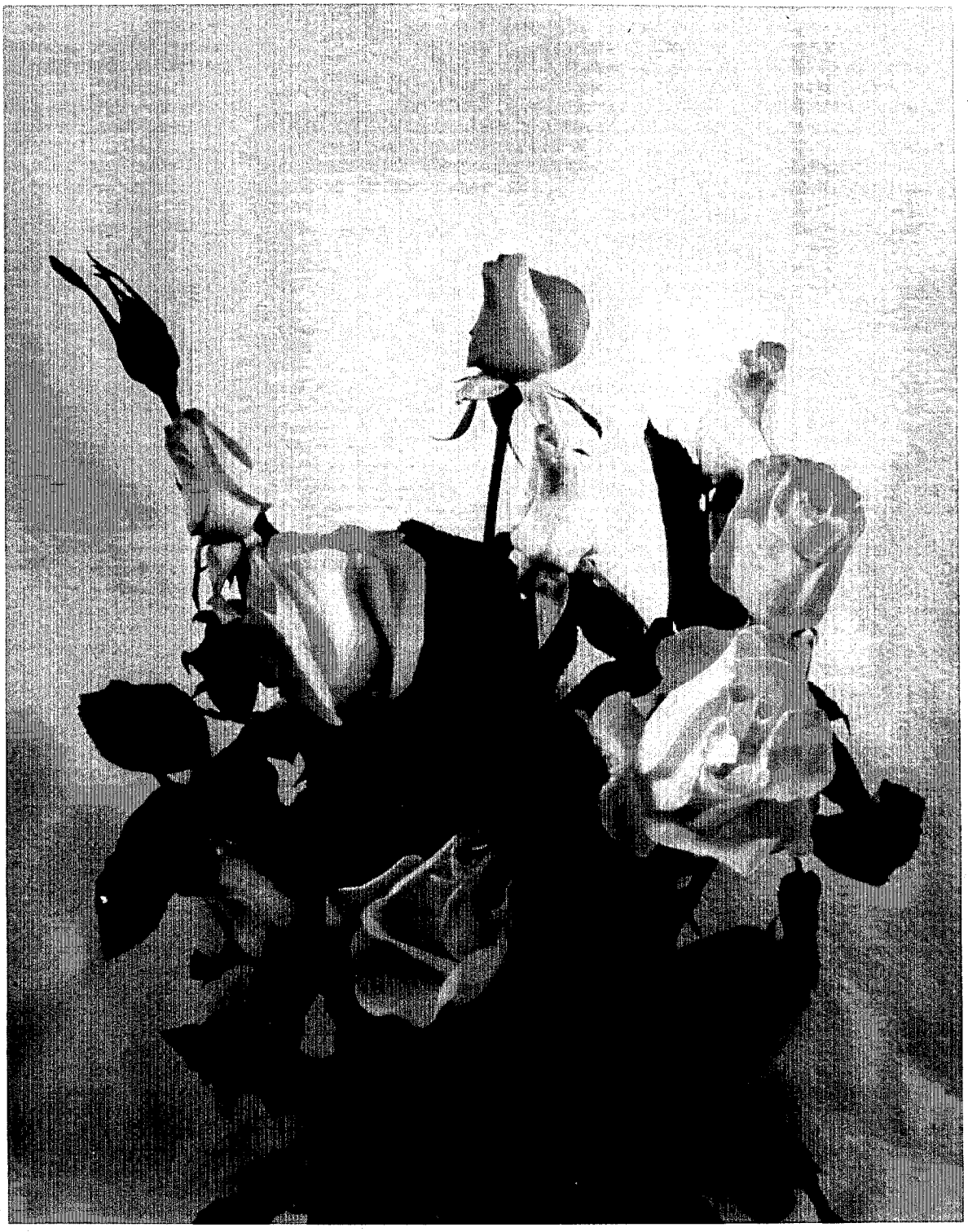

* * * * *